(12) United States Patent
Michelet et al.

(10) Patent No.: US 8,729,254 B2
(45) Date of Patent: May 20, 2014

(54) DERIVATIVE OF GLUCOSE AND VITAMIN F, COMPOSITIONS COMPRISING IT, USES AND PREPARATION PROCESS

(75) Inventors: Jean-François Michelet, Creteil (FR); Maria Dalko, Gif S/Yvette (FR); Bruno Bernard, Neuilly sur Seine (FR); Didier Semeria, Livry-Gargan (FR); Michel Philippe, Wissous (FR)

(73) Assignee: L'Oreal, Paris (FR)

( * ) Notice: Subject to any disclaimer, the term of this patent is extended or adjusted under 35 U.S.C. 154(b) by 432 days.

(21) Appl. No.: 12/370,006

(22) Filed: Feb. 12, 2009

(65) Prior Publication Data

US 2009/0149396 A1 Jun. 11, 2009

Related U.S. Application Data

(62) Division of application No. 11/393,829, filed on Mar. 31, 2006, now Pat. No. 7,977,318, which is a division of application No. 10/459,539, filed on Jun. 12, 2003, now Pat. No. 7,763,587.

(60) Provisional application No. 60/390,440, filed on Jun. 24, 2002, provisional application No. 60/390,445, filed on Jun. 24, 2002.

(30) Foreign Application Priority Data

Jun. 13, 2002 (FR) .................................. 02 07290
Jun. 13, 2002 (FR) .................................. 02 07293

(51) Int. Cl.
| | | |
|---|---|---|
| C07H 13/06 | (2006.01) |
| C07H 1/00 | (2006.01) |
| A61K 8/34 | (2006.01) |
| A61K 8/73 | (2006.01) |
| A61K 31/133 | (2006.01) |
| A61K 31/192 | (2006.01) |
| A61K 31/4412 | (2006.01) |
| A61K 31/7024 | (2006.01) |
| A61K 31/717 | (2006.01) |
| A61Q 7/00 | (2006.01) |
| A61Q 5/02 | (2006.01) |
| A61Q 5/00 | (2006.01) |

(52) U.S. Cl.
CPC .................. *C07H 13/06* (2013.01); *C07H 1/00* (2013.01); *A61K 31/133* (2013.01); *A61K 31/192* (2013.01); *A61K 31/4412* (2013.01); *A61K 31/7024* (2013.01); *A61K 31/717* (2013.01); *A61Q 7/00* (2013.01); *A61Q 5/02* (2013.01); *A61Q 5/006* (2013.01); *A61K 8/34* (2013.01); *A61K 8/731* (2013.01); *Y10S 514/88* (2013.01)

USPC .............................. 536/124; 514/23; 514/880

(58) Field of Classification Search
None
See application file for complete search history.

(56) References Cited

U.S. PATENT DOCUMENTS

| | | | | |
|---|---|---|---|---|
| 3,862,121 | A * | 1/1975 | Jaques et al. ................. | 536/18.2 |
| 4,393,043 | A * | 7/1983 | Koulbanis et al. .............. | 424/59 |
| 5,268,180 | A * | 12/1993 | Morancais et al. ............ | 424/450 |
| 5,496,565 | A * | 3/1996 | Heinze et al. ................. | 424/502 |
| 5,550,225 | A * | 8/1996 | Philippe ........................ | 536/115 |
| 6,562,977 | B2 * | 5/2003 | Karpf et al. ................... | 546/170 |
| 6,858,216 | B2 * | 2/2005 | Schulze zur Wiesche et al. ............................ | 424/401 |

FOREIGN PATENT DOCUMENTS

WO    WO 98/52528    * 11/1998

OTHER PUBLICATIONS

Smith, C. et al "A double blind, randomized control clinical trial . . ." Clin. Dermatolog. (2000) vol. 25, pp. 580-583.*
STN Registry entry for "Vitamin F" accessed Jan. 30, 2009.*
Wikipedia entry for "Essential fatty acids" accessed Jan. 30, 2009.*
Reinefeld, V. et al "Selektive acylierung von D-glucose" Starke (1968) vol. 20, No. 6, pp. 181-189.*
English translation of Reinefeld, V. et al Die Starke (1968) vol. 20, No. 6, pp. 181-189.*

* cited by examiner

*Primary Examiner* — Leigh Maier
(74) *Attorney, Agent, or Firm* — Novak Druce Connolly Bove + Quigg LLP

(57) ABSTRACT

An O-acyl product derived from glucose which may be obtained by partial or total esterification of glucose and of vitamin F, comprising a mixture of esters, for example, monoesters, of glucose and of at least one acid chosen from linoleic acid, oleic acid, palmitic acid and stearic acid, compositions, for example, cosmetic and pharmaceutical compositions, comprising this novel derivative, and their use for improving the condition of head hair and/or other hairs, and, for example, for reducing and/or impeding the loss of head hair and/or other hairs, and/or for inducing and/or stimulating hair growth, as well as a process for preparing O-acyl derivatives mainly in position 6 of glucose, comprising preparing a mixed anhydride by reacting a carboxylic acid with a trimethylacetyl halide, followed by reacting said mixed anhydride formed with glucose.

15 Claims, No Drawings

DERIVATIVE OF GLUCOSE AND VITAMIN F, COMPOSITIONS COMPRISING IT, USES AND PREPARATION PROCESS

This is a division of application Ser. No. 11/393,829, filed Mar. 31, 2006, now U.S. Pat. No. 7,977,318 which is a division of application Ser. No. 10/459,539, filed Jun. 12, 2003, now U.S. Pat. No. 7,763,587 and claims the benefit of U.S. Provisional Application No. 60/390,440, filed Jun. 24, 2002, and the benefit of U.S. Provisional Application No. 60/390,445, filed Jun. 24, 2002, all of which are incorporated herein by reference.

Disclosed herein are novel O-acyl derivatives of glucose, their use, for example, in cosmetics or in pharmaceuticals, for example, for combating hair loss, and compositions, for example, cosmetic or pharmaceutical compositions, comprising at least one of these derivatives. Further disclosed herein is a novel process for preparing the glucose derivatives, said derivatives being O-acylated mainly in position 6 of the glucose.

In human beings, hair growth and its renewal can mainly be determined by the activity of the hair follicles and their dermo-epidermal environment. Their activity can be cyclic and essentially can comprise three phases, namely the anagenic phase, the catagenic phase and the telogenic phase.

The active anagenic phase or growth phase, which can last several years and in the course of which the hair gets longer, is followed by a very short and transient catagenic phase which can last a few weeks, and then by a rest phase, known as the telogenic phase, which can last a few months.

At the end of the rest period, the hairs fall out and a new cycle starts. The hair is thus in constant renewal and, out of the approximately 150,000 hairs which make up a head of hair, at any moment, about 10% of them are at rest and will thus be replaced within a few months.

In a large number of cases, early loss of hair can occur in individuals who are genetically predisposed, and this, for example, can affect men. This, for example, involves androgenetic or androgenic alopecia or androgeno-genetic alopecia.

This alopecia can essentially be due to a disruption in hair renewal, which can result, in a first stage, in acceleration of the frequency of the cycles at the expense of the quality and then the quantity of the hairs. A gradual thinning of the head of hair can take place by regression of the so-called "terminal" hairs at the downy stage. Certain regions can preferentially be affected, for example, the temporal or frontal areas and the upper part of the occipital bone in men, and a diffuse alopecia of the vertex can be observed in women.

Substances for suppressing or reducing the effect of alopecia, for example, for reducing or slowing down hair loss or for inducing or stimulating the growth of head hairs and/or other hairs, have been sought for many years, for example, in the cosmetics industry.

In this respect, a large number of very diverse active compounds has already been proposed, such as 2,4-diamino-6-piperidinopyrimidine 3-oxide, or "Minoxidil", and also the many derivatives thereof.

Oligosaccharides containing at least one disaccharide unit comprising a uronic acid residue and a hexosamine residue have also been proposed, for example, in EP 211 610.

Patent application WO-A-93/02657 teaches that compounds of alkylpolyglycoside type and/or O-acyl derivatives of glucose may make it possible to induce and stimulate hair growth and to reduce hair loss effectively. This patent application WO-A-93/02657, for example, describes the use of derivatives corresponding to the formula:

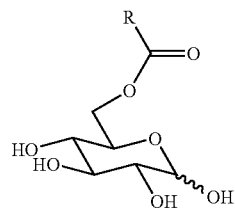

wherein R is chosen from saturated and unsaturated, linear hydrocarbon-based chains comprising from 7 to 19 carbon atoms,
for combating hair loss or for stimulating hair growth, for example, in cosmetics or pharmaceuticals.

This document WO-A-93/02657 mentions, inter alia, the use of derivatives wherein the acyl residue RCO— is chosen from octanoyl, decanoyl, dodecanoyl, myristoyl, hexadecanoyl, stearoyl, oleoyl, linoleoyl and linolenoyl residues.

For example, the radicals mentioned and given as examples are the octanoyl and oleoyl radicals.

It remains, in general, that it would be advantageous and useful to have available active compounds other than those already known, which can be potentially more active and/or less toxic, and which may be used in the cosmetics field.

After extensive research, the inventors have now demonstrated that, surprisingly and unexpectedly, a certain novel product, an O-acyl derivative of glucose, has at least one of the following noteworthy properties capable of justifying its use for improving the condition of the hair reducing the loss of head hair and/or other hairs, impeding the loss of head hair and/or other hairs, inducing hair growth, and stimulating hair growth.

For example, the product disclosed herein can have the advantage of being composed mainly of essential fatty acid derivatives naturally present in the human body.

This product can also be more stable over time than the free fatty acids it comprises.

Finally, it can be easy to synthesize at an industrial level, and can be synthesized relatively inexpensively.

Disclosed herein is thus an O-acyl product derived from glucose which may be obtained by partial or total esterification of vitamin F with at least one hydroxy group of glucose.

Further disclosed herein is a composition comprising, in a physiologically acceptable medium, at least one O-acyl product as defined above.

Further disclosed herein is a cosmetic process for treating head hairs and/or other hairs, comprising applying to skin, the head hair and/or other hairs a cosmetic composition as defined above.

Even further disclosed herein is a cosmetic process for treating head hairs and/or other hairs, comprising applying to skin, the head hair and/or other hairs a cosmetic composition comprising an effective amount of at least one O-acyl product as defined above, leaving the composition in contact with the head hair and/or other hairs, and optionally rinsing the composition out.

Further disclosed herein is the use of at least one O-acyl product as defined above for the preparation of a composition, for example, a pharmaceutical composition, for improving the condition of head hair and/or other hairs, and which, for example, may be intended for achieving at least one effect chosen from reducing the loss of head hair and/or other hairs, impeding the loss of head hair and/or other hairs, inducing hair growth, and stimulating hair growth.

It is known to those skilled in the art that vitamin F, a compound naturally present in fatty substances and, for example, in linseed oil, sunflower oil or safflower oil, comprises a mixture of fatty acids, for example, chosen from fatty acids comprising from $C_{12}$ to $C_{20}$ hydrocarbon-based chains.

Thus, vitamin F can be considered to comprise, for example, (% by weight):
from 75% to 80% by weight of linoleic acid,
from 10% to 15% by weight of oleic acid,
from 4% to 8% by weight of palmitic acid,
from 0.5% to 3% by weight of stearic acid, and
from 0 to 10% by weight of at least one other acid chosen from lauric acid, myristic acid, arachidic acid, behenic acid, lauroleic acid, myristoleic acid, palmitoleic acid and linolenic acid.

It results therefrom that the product disclosed herein, which may be obtained by esterification of vitamin F, thus itself can comprise a mixture of different esters, deriving from the presence of the various acids, that can be formed during this reaction.

Moreover, since glucose comprises five sites capable of reacting during the esterification reaction, the product disclosed herein thus also comprises a mixture of the esters formed on the various positions of glucose.

Finally, the product disclosed herein also comprises a mixture of the monoesters and diesters that may be formed during esterification.

As used herein, the expression "product" disclosed herein therefore means a mixture comprising all the monoesters and/or diesters formed during the esterification reaction of vitamin F and glucose.

The product disclosed herein thus comprises a mixture of compounds that may, for example, be chosen from at least one compound of formula (I) below:

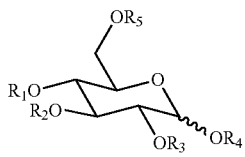

wherein:
$R_1$, $R_2$, $R_3$, $R_4$ and $R_5$, which may be identical or different, are each chosen from hydrogen and radicals —CO—R wherein R is chosen from saturated and unsaturated, linear hydrocarbon-based chains comprising from 11 to 21 carbon atoms, with the proviso that at least one of the radicals $R_1$ to $R_5$ is not hydrogen.

The ratio of the number of ester functional groups in the esterified product to the number of initial hydroxyl functional groups, or degree of esterification, per glucose molecule may range, for example, from 0.2 to 1, further, for example, from 0.2 to 0.6 and even further, for example, from 0.21 to 0.4.

Moreover, the glucose may, for example, be esterified in at least one position chosen from position 1, position 2, position 3 and position 6. In one embodiment, the glucose can be esterified in at least one position chosen from position 1 and position 6.

The ratio of the number of ester functional groups in position 6 to the total number of ester functional groups, per glucose molecule, can range, for example, from 0.55:1 to 1:1, further, for example, from 0.70:1 and 0.98:1 and, even further, for example, from 0.90:1 and 0.97:1.

The product disclosed herein may comprise at least one ester, for example, at least one monoester, of glucose and of linoleic acid; at least one ester, for example, at least one monoester, of glucose and of oleic acid; at least one ester, for example, at least one monoester, of glucose and of palmitic acid; and at least one ester, for example, at least one monoester, of glucose and of stearic acid.

It may also comprise at least one ester, for example, at least one monoester, of glucose and of at least one acid chosen from lauric acid, myristic acid, arachidic acid, behenic acid, lauroleic acid, myristoleic acid, palmitoleic acid and linolenic acid.

It may also comprise at least one diester of glucose and of at least one acid chosen from lauric acid, myristic acid, arachidic acid, behenic acid, lauroleic acid, myristoleic acid, palmitoleic acid, linoleic acid, oleic acid, palmitic acid, stearic acid and linolenic acid.

Thus, in one embodiment, the product disclosed herein may comprise, for example, all positions considered together:
from 40% to 80% by weight, for example, from 60% to 75% by weight and further, for example, from 68 to 72% by weight of at least one monoester of glucose and of linoleic acid,
from 10% to 20% by weight, for example, from 12% to 17% by weight and further, for example, from 14 to 15%, by weight of at least one monoester of glucose and of oleic acid,
from 5% to 20% by weight, for example, from 7% to 15% by weight and further, for example, from 9 to 12% by weight of at least one monoester of glucose and of palmitic acid,
from 0.5% to 7% by weight, for example, from, 1% to 5% by weight and further, for example, from 2 to 4% by weight of at least one monoester of glucose and of stearic acid,
from 0 to 10% by weight, for example, from 0.10 to 4% by weight and further, for example, from 0.15 to 2% by weight of at least one monoester of glucose and of at least one acid chosen from lauric acid, myristic acid, arachidic acid, behenic acid, lauroleic acid, myristoleic acid, palmitoleic acid and linolenic acid,
0 to 10% by weight, for example, from 0.10 to 4% by weight and further, for example, from 0.15 to 2% by weight, of at least one diester of glucose and of at least one acid chosen from lauric acid, myristic acid, arachidic acid, behenic acid, lauroleic acid, myristoleic acid, palmitoleic acid, linoleic acid, oleic acid, palmitic acid, stearic acid and linolenic acid.

In another embodiment, the product disclosed herein may comprise:
from 40% to 80% by weight, for example, from 60% to 75% by weight and further, for example, from 68 to 72% by weight of at least one ester of glucose and of linoleic acid, for example, chosen from 6-O-octadeca-9,12-dienoyl-D-glucopyranose, 1-O-octadeca-9,12-dienoyl-D-glucopyranose, 2-O-octadeca-9,12-dienoyl-D-glucopyranose and 3-O-octadeca-9,12-dienoyl-D-glucopyranose,
from 10% to 20% by weight, for example, from 12% to 17% by weight and further, for example, from 14 to 15% by weight of at least one ester of glucose and of oleic acid, for example, chosen from 6-O-octadeca-9-enoyl-D-glucopyranose, 3-O-octadeca-9-enoyl-D-glucopyranose, 1-O-octadeca-9-enoyl-D-glucopyranose and 2-O-octadeca-9-enoyl-D-glucopyranose,
from 5% to 20% by weight, for example, 7% to 15% by weight and further, for example, from 9 to 12% by weight of at least one ester of glucose and of palmitic acid, for example, chosen from 6-O-hexadecanoyl-D-glucopyranose, 3-O-hexadecanoyl-D-glucopyranose, 1-O-hexadecanoyl-D-glucopyranose and 2-O-hexadecanoyl-D-glucopyranose, from 0.5% to 7% by weight, for example, from 1% to 5% by weight and further, for example, from 2 to 4% by weight of at least one ester of glucose and of stearic acid, for example, chosen from 6-O-octadecanoyl-D-glucopyranose, 3-O-octadecanoyl-D-glucopyranose, 1-O-octadecanoyl-D-glucopyranose and 2-O-octadecanoyl-D-glucopyranose, from 0 to 10% by weight, for example, from 0.10 to 4% by weight, and even further, for example, from 0.15 to 2% by weight, of at least one ester of glucose and of at least one acid chosen from lauric acid, myristic acid, arachidic acid, behenic acid, lauroleic acid, myristoleic acid, palmitoleic acid and linolenic acid, 0 to 10% by weight, for example, from 0.10 to 4% by weight, even further, for example, from 0.15 to 2% by weight, of at least one diester of glucose and of at least one acid chosen from lauric acid, myristic acid, arachidic acid, behenic acid, lauroleic acid, myristoleic acid, palmitoleic acid, linoleic acid, oleic acid, palmitic acid, stearic acid and linolenic acid.

The esterification reaction may, for example, be performed according to any known method. The synthesis may, for example, be performed starting with the acid chloride (vitamin F chloride) and D-glucose, according to the method described by Reinefeld et al. in "*Die Stärke*" No. 6, pages 181-189, 1968.

For example, Reinefeld et al. described and compared several methods for esterifying D-glucose with lauric acid.

Among the agents for acylating glucose, it has been proposed to use acid chlorides, acid imidazolides, carboxylic-carbonic mixed anhydrides and carboxylic anhydrides. In the case of the transesterification reactions, the agents used can be the methyl or ethyl esters of the acids.

It emerges from Reinefeld et al. that the method that can allow the highest yield to be obtained is acylation using the acid chloride. For example, with lauroyl chloride, a mixture of monoester and diesters can be obtained, in a yield of 49%, including 36% for the monoester.

This method was, for example, used in patent EP 0485251 to give 6-O-acyl glucoses in a yield, for example, of 40% with oleyl chloride.

However, it may not always be easy to obtain the appropriate acid chloride. In the absence of industrial acid chloride, it then may be necessary to use another method.

Acylation using acid imidazolides can lead to a mixture of monoesters and diesters, in a total yield of 22% and a yield of 9% for the monoesters alone, when lauric acid imidazolide is used.

The acylation of glucose by means of forming the true anhydride can lead to the desired compounds in a total yield of 46% for the mixture of monoester and diesters, and of 28% for the production of the monoesters.

This process may give rise to the formation of free fatty acids that may need to be removed in order to lead to relatively pure end products.

However, this removal may occasionally prove to be difficult, given the nature of the impurities. Moreover, it is generally sought to avoid the intermediate purification steps, which can needlessly lengthen the process and can generate additional costs, this being incompatible with an industrial process.

It has been found that, irrespective of the method envisaged, the acylating agent chosen and/or the proportion of each of the reagents, the acylation of glucose could always lead to the production of a mixture in which it was possible to identify D-glucopyranose 6-ester, but also D-glucopyranose 1,6-diester and D-glucopyranose 2,6-diester as co-existing reaction products.

There is thus still the need for a novel route for the synthesis of O-acyl derivatives of glucose, which can allow the production of these compounds quickly and easily at the industrial level, with a large yield of desired products.

Therefore, the present inventors sought to overcome at least one of these drawbacks of the prior art and to propose a process which can allow the preparation of said O-acyl derivatives of glucose in a minimum yield of about 70%.

Moreover, it has been found that the novel process disclosed herein can also make it possible to selectively obtain glucose esters mainly in position 6.

In addition, this process can allow the use of industrial acid chlorides.

Disclosed herein is thus a process for preparing at least one O-acyl derivative mainly in position 6 of glucose, chosen from derivatives of formula (Ia):

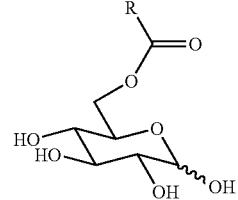

(Ia)

wherein R is chosen from saturated and unsaturated, linear and branched hydrocarbon-based chains comprising from 7 to 21 carbon atoms, comprising:

preparing a mixed anhydride of formula (II):

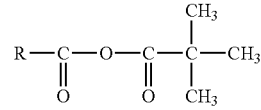

(II)

by reacting a carboxylic acid of formula R—COOH with a trimethylacetic acid halide of formula X—C(O)—C(CH$_3$)$_3$, wherein X may, for example, be chosen from chlorine and bromine, and reacting said mixed anhydride formed with glucose.

The process disclosed herein can, for example, make it possible to prepare the at least one O-acyl derivative of glucose mainly in position 6 chosen from derivatives of formula (Ia). The process disclosed herein may also make it possible, for example, to prepare the O-acyl product derived from glucose which may be obtained by partial or total esterification of glucose and of vitamin F.

For example, the radical R can be chosen from saturated and unsaturated, linear and branched hydrocarbon-based chains comprising from 11 to 17 carbon atoms.

The acyl residue —COR may, for example, be chosen from octanoyl, decanoyl, dodecanoyl, myristoyl, hexadecanoyl, stearoyl, palmitoleoyl, oleoyl, linoleoyl and linolenoyl residues.

The process disclosed herein thus comprises, in a first step, for example, preparing a mixed anhydride of formula (II), by reacting a carboxylic acid of formula R—COOH with a trimethylacetic acid halide of formula X—C(O)—C(CH$_3$)$_3$, wherein X, for example, is chosen from chlorine and bromine.

The carboxylic acids that may be used in the process disclosed herein, may, for example, be chosen from at least one of octanoic acid, decanoic acid, dodecanoic acid, myristic acid, hexadecanoic acid, stearic acid, oleic acid, linoleic acid and linolenic acid.

The reaction scheme is then as follows:

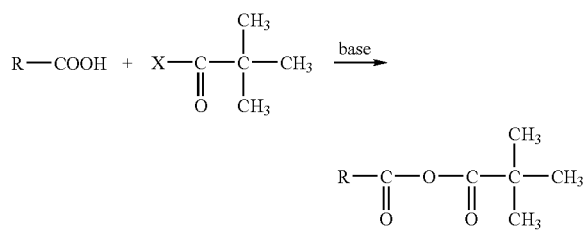

The reaction may be performed in an organic reaction solvent, such as an organic reaction solvent chosen from at least one of tetrahydrofuran, N,N-dimethylformamide, N-methylpyrrolidone, pyridine and toluene, It may, for example, be performed under an inert atmosphere, for example, under nitrogen.

At least one base may be used to activate the carboxylic acid, or the corresponding carboxylate may be used directly; this at least one base may, for example, be chosen from organic bases chosen, for example, from at least one of triethylamine, pyridine, 4-dimethylaminopyridine, tributylamine and N-methylmorpholine. The reaction may be performed at a temperature ranging, for example, from −25° C. to +40° C. and further, for example, from −10° C. to +10° C., and, for example, for a duration ranging from 5 minutes to 5 hours, further, for example, from 30 minutes to 3 hours.

For example, from 0.3 to 3 equivalents and further, for example, from 0.5 to 1.5 equivalents of carboxylic acid can be reacted with 1 equivalent of trimethylacetic acid halide.

In the esterification step of the process, said mixed anhydride can be reacted with glucose. This esterification may optionally be performed after suction-filtering the salts possibly formed during the previous reaction.

This esterification may, for example, be performed in an organic reaction solvent, which may be the same organic reaction solvent as that used in the preparation of the mixed anhydride of formula (II). This organic reaction solvent may, for example, be chosen from at least one of tetrahydrofuran, N,N-dimethylformamide, N-methylpyrrolidone, pyridine and toluene.

The mixed anhydride may, for example, be dissolved in said organic reaction solvent before reaction.

For example, the glucose can be dissolved beforehand in a solvent chosen from at least one of pyridine, dimethylformamide, N-methylpyrrolidone and dimethylacetamide.

For example, from 0.5 to 1.5 equivalents, further, for example, from 0.9 to 1.1 equivalents and even further, for example, 1 equivalent of mixed anhydride can be reacted with 3 equivalents of glucose.

At least 3 equivalents of glucose may, for example, be used relative to the acid or the mixture of acids reacted in the previous reaction.

The esterification may be performed at a temperature ranging, for example, from −25° C. to +100° C., further, for example, from 0° C. to +60° C. and even further, for example, from 20 to 25° C., and for a duration ranging, for example, from 1 to 30 hours, and further, for example, from 2 to 15 hours.

After the esterification, the solvents may be separated from the desired product, for example, by evaporation, centrifugation or filtration.

The resulting product may be purified by any known means, such as distillation, chromatography on a column of silica gel, precipitation and/or extraction, for example, with a water/organic solvent mixture.

The process disclosed herein thus can make it possible in an industrially achievable manner to prepare at least one O-acyl derivative of glucose, mainly in position 6. For example, at least one of the following O-acyl derivatives of glucose may be prepared according to this process: 6-O-octadeca-9,12-dienoyl-D-glucopyranose; 6-O-octadeca-9-enoyl-D-glucopyranose; 6-O-octadecanoyl-D-glucopyranose; and 6-O-hexadecanoyl-D-glucopyranose.

It has been found that, for example, with the process disclosed herein, glucose can mainly be esterified in position 6, and possibly in at least one position chosen from 1, 2, and 3 positions.

The ratio of the number of ester functional groups in position 6 to the total number of ester functional groups per glucose molecule can range, for example, from 55% to 95%, further, for example, from 60% to 80% and even further, for example, from 68 to 75%.

At least one O-acyl product derived from glucose disclosed herein may be used, for example, in a composition or for the preparation of a composition that moreover comprises a physiologically acceptable medium. This composition may, for example, be in the form of a cosmetic composition that therefore comprises a cosmetically acceptable medium or, for example, in the form of a pharmaceutical composition that therefore comprises a pharmaceutically acceptable medium.

The amount of the at least one O-acyl product to be used in the compositions disclosed herein may readily be determined by a person skilled in the art, for example, on the basis of the nature of the composition and/or the desired effect.

For example, this amount may range, for example, from 0.01 to 20% by weight, relative to the total weight of the composition, further, for example, from 0.1 to 10% by weight, relative to the total weight of the composition, and even further, for example, from 0.5 to 5% by weight, relative to the total weight of the composition.

The physiologically, cosmetically or pharmaceutically acceptable medium in which the product disclosed herein may be used can readily be determined by a person skilled in the art. It is a medium that is compatible with application to a keratin material such as the eyelashes, the eyebrows, head hair and/or other hairs.

The medium may be anhydrous or aqueous.

The term "anhydrous medium" means a solvent medium comprising less than 1% by weight of water. An anhydrous medium may comprise, for example, at least one organic solvent chosen, for example, from $C_1$-$C_4$ alcohols, such as ethanol; alkylene glycols, such as propylene glycol; alkylene glycol and dialkylene glycol alkyl ethers, wherein the alkyl and alkylene radicals comprise from 1 to 4 carbon atoms.

The term "aqueous medium" means a medium comprising water or a mixture of water and at least one other physiologically acceptable solvent chosen, for example, from the at least one organic solvent mentioned above. In the latter case, the at least one other physiologically acceptable solvent may, for example, be present in an amount ranging from 5% to 95% by weight, relative to the total weight of the composition.

It is possible to add to the composition, comprising the at least one O-acyl product disclosed herein, at least one agent chosen from cosmetic and pharmaceutical active agents, for example, chosen from at least one of:

compounds for improving the activity with respect to regrowth of the hair and/or impeding hair loss, and which have already been described for this activity, such as nicotinic acid esters, for example, chosen from tocopheryl nicotinate, benzyl nicotinate and $C_1$-$C_6$ alkyl nicotinates such as methyl and hexyl nicotinate; pyrimidine derivatives, for example, 2,4-diamino-6-piperidinopyrimidine 3-oxide or "Minoxidil" described in U.S. Pat. Nos. 4,139,619 and 4,596,812; pyrimidine 3-oxide derivatives, for example, those described in documents WO 92/01437 and WO 96/09048, and, for example, "Aminexil" or 2,4-diaminopyrimidine 3-N-oxide;

antibacterial agents such as macrolides, pyranosides and tetracyclins, and, for example, erythromycin;

calcium antagonists, for example, cinnarizine, diltiazem, nimodipine and nifedipine;

hormones such as oestriol and the analogues thereof, vitamin D and the analogues thereof, and thyroxin and the salts thereof;

steroidal and non-steroidal antiinflammatory agents, such as corticosteroids, for example, hydrocortisone;

antiandrogens, such as oxendolone, spironolactone, diethylstilbestrol and flutamidem;

steroidal and non-steroidal inhibitors of 5-α-reductases, such as finasteride and 4,6-dimethoxyindole-2-carboxylic acid and the derivatives thereof as described in European Patent No. 1 068 858;

potassium agonists such as cromakalim and nicorandil, retinoid RXR receptor agonists and retinoid antagonists;

OH-radical scavengers such as dimethyl sulphoxide;

peptides, for example, the tripeptide Lys-Pro-Val, and for example, α-MSH and the derivatives thereof;

antidandruff and antifungal agents such as zinc pyrithione, piroctone olamine, selenium disulphide, tropolone, hinokitiol, hinokitiol-zinc and hinokitiol-copper complexes described, for example, in European Patent No. 0 728 478, and divalent metal complexes such as those described in French Patent No. 01/03309; and free-radical scavengers; anti-seborrhoeic agents; antiparasitic agents; antiviral agents; anti-pruriginous agents.

The cosmetic and pharmaceutical active agents may also, for example, be chosen from at least one of: diazoxide, spiroxazone, phospholipids, for example, lecithin, linoleic acid and linolenic acid; salicylic acid and the derivatives thereof described in French Patent No. 2 581 542, for example, salicylic acid derivatives bearing at least one alkanoyl group comprising from 2 to 12 carbon atoms in position 5 of the benzene ring; hydroxycarboxylic acids and keto carboxylic acids and the esters thereof; lactones and the corresponding salts thereof; anthralin, carotenoids; eicosatetraenoic acid and eicosatrienoic acid and the esters and amides thereof; and extracts of plant and bacterial origin.

At least one adjuvant commonly used in the field of application under consideration, for example, in cosmetics, may moreover be added to the physiologically acceptable medium, such as at least one adjuvant chosen from surfactants, emulsifiers, hydrophilic and lipophilic thickeners and gelling agents, cosmetic agents, preserving agents, solvents, antioxidants, UV screening agents, acidifying and basifying agents, oils and waxes of animal, mineral, plant and synthetic origin, fillers, and dyestuffs such as pigments and colorants; these adjuvants are well known in the prior art.

The nature and amount of the at least one adjuvant may be chosen by a person skilled in the art on the basis of his or her general knowledge, so as to obtain the presentation form desired for the composition. In any case, a person skilled in the art will take care to select all the optional additional compounds and/or the amount thereof such that the advantageous properties of the composition disclosed herein are not, or are not substantially, adversely affected by the envisaged addition(s).

The oils or waxes that may be used in the composition disclosed herein, may, for example, be chosen from at least one of mineral oils (liquid petroleum jelly), plant oils (liquid fraction of karite butter, sunflower oil), animal oils (perhydrosqualene), synthetic oils (purcellin oil), silicone oils and waxes (cyclomethicone) and fluoro oils (perfluoropolyethers), beeswax, carnauba wax and paraffin wax. At least one of fatty alcohols and fatty acids, such as stearic acid may, can also be added to the oils.

The emulsifiers that can be used in the composition disclosed herein may, for example, be chosen from at least one of glyceryl stearate, polysorbate 60 and the mixture of PEG-6/PEG-32/glycol stearate sold under the name Tefose 63 by the company Gattefosse.

The solvent that may be used in the composition disclosed herein may, for example, be chosen from lower alcohols, for example, ethanol and isopropanol, and propylene glycol.

The hydrophilic gelling agents that may be used in the composition disclosed herein may, for example; be chosen from at least one of carboxyvinyl polymers (carbomer), acrylic copolymers such as acrylate/alkylacrylate copolymers, polyacrylamides, polysaccharides such as hydroxypropylcellulose, natural gums and clays. The lipophilic gelling agents that may be used in the composition disclosed herein may, for example, be chosen from at least one of modified clays, for example, bentones, metal salts of fatty acids, for example, aluminium stearates and hydrophobic silica, ethylcellulose and polyethylene.

The compositions that may be used according to the embodiments disclosed herein may comprise other hydrophilic cosmetic and pharmaceutical active agents, for example, chosen from at least one of proteins and protein hydrolysates, amino acids, polyols, urea, allantoin, sugars and sugar derivatives, water-soluble Vitamins, plant extracts and hydroxy acids.

The lipophilic cosmetic or pharmaceutical active agents that may be used in the compositions disclosed herein may, for example, be chosen from at least one of retinol (vitamin A) and the derivatives thereof, tocopherol (vitamin E) and the derivatives thereof, essential fatty acids, ceramides, essential oils, and salicylic acid and the derivatives thereof.

The compositions disclosed herein may, for example, be in any presentation form normally used.

The compositions may, for example, be in a form chosen from aqueous and oily solutions and dispersions of lotion and serum type; emulsions of liquid and semi-liquid consistency of the milk type, oil-in-water, water-in-oil and multiple emulsions; suspensions and emulsions of soft consistency of the aqueous and anhydrous cream and gel type; microcapsules and microparticles; vesicular dispersions of ionic and/or nonionic type. It may also be used in a form chosen from aqueous, alcoholic and aqueous-alcoholic solutions, creams, gels, emulsions and mousses, or in a form chosen from aerosol compositions further comprising at least one propellant under pressure.

The composition disclosed herein may, for example, be chosen from haircare compositions, for example, shampoos, medicated lotions and creams, hair setting lotions, styling creams and gels; dye compositions, for example, oxidation dye compositions, optionally in the form of coloring shampoos; restructuring lotions for the hair; permanent-waving compositions (for example, compositions for the first stage of a permanent-waving operation); lotions and gels for preventing hair loss; and antiparasitic shampoos.

The compositions disclosed herein may, for example, be applied to an individual's alopecic areas, and then may, for example, optionally be left in contact for several hours and may, for example, optionally be rinsed out.

The composition comprising an effective amount of the product disclosed herein may, for example, be applied in the evening; it may, further, for example, be kept in contact throughout the night and a shampoo wash may, even further, for example, optionally be performed in the morning Further disclosed herein is a cosmetic process for treating head hairs and/or other hairs, comprising applying to skin, the head hair and/or other hairs a cosmetic composition comprising an effective amount of the product disclosed herein, leaving the composition in contact with the head hair and/or other hairs, and optionally rinsing the composition out.

The treatment process can have the characteristics of a cosmetic-process in so far as it can make it possible to enhance the aesthetic appearance of head hairs and/or other hairs, for example, by giving them greater vigour and/or improving their appearance.

The embodiments disclosed herein are illustrated in greater detail in the examples that follow without, however, being limiting in nature.

In these examples, the compounds 6-O-octadeca-9-enoyl-D-glucopyranose and 6-O-hexadecenoyl-D-glucopyranose were prepared according to the method described in European Patent No. 485 251.

The compounds 6-O-octadeca-9,12-dienoyl-D-glucopyranose and 6-O-octadecanoyl-D-glucopyranose were described in the literature.

EXAMPLE 1

Preparation of the Glucose Ester of Vitamin F (Mainly Ester in Position 6)

17 ml of trimethylacetyl chloride was diluted in 100 ml of tetrahydrofuran in a 500 ml three-necked flask; a mixture of 37.3 g of vitamin F and 19.3 ml of triethylamine predissolved in 100 ml of tetrahydrofuran was added, under an inert atmosphere and at 0° C.; the mixture was stirred for 1 hour and the salts formed were then filtered off to give a solution.

96 g of D-glucose was dissolved in 1.15 liters of pyridine in a 2 liter three-necked flask, and the above solution was added thereto, under an inert atmosphere, at room temperature. The mixture was stirred overnight.

The reaction medium was evaporated to dryness under vacuum to remove the pyridine, the paste obtained was extracted (water/organic solvent mixture) and the organic phase recovered was dried, filtered and evaporated.

49 g of a yellow paste (yield: 83%) of vitamin F ester were obtained, including 72% of monoesters (mixture) in position 6.

$^1$H NMR spectrum (DMSO) 200 MHz: δ (ppm): 0.85; 1.23; 1.50; 2.00; 2.26; 2.73; 3.03; 3.13; 3.40; 3.76; 3.97; 4.25; 4.53; 4.76; 4.89; 5.04; 5.32; 6.34.

$^{13}$C NMR spectrum (DMSO) 200 MHz: δ (ppm): 13.95; 22.12; 24.48; 25.23; 26.62; 28.46 to 29.08; 31.32; 33.44; 63.91; 69.14; 70.57; 72.19; 72.86; 92.30; 127.77; 129.73; 172.92.

The $^1$H and $^{13}$C NMR spectra (DMSO) 200 MHz were in accordance with the expected structure.

EXAMPLE 2

Preparation of the Glucose Ester of Vitamin F (Mainly Ester in Position 3)

20 g of vitamin F dissolved in 300 ml of anhydrous toluene was introduced into a 500 ml round-bottomed flask, under a nitrogen atmosphere, and 3 drops of DMF was added thereto to catalyze the reaction. 12.6 ml of oxalyl chloride was then added dropwise (evolution of gas) and the mixture was stirred at 25° C. for 3 hours. The reaction medium was concentrated to the maximum and then diluted in 200 ml of dichloromethane. Vitamin F chloride was thus obtained, which was used in the following step.

29.6 g of diacetone-D-glucose dissolved in 200 ml of dichloromethane, and 26 ml of triethylamine, were introduced into a 500 ml three-necked flask on which was mounted a condenser and a dropping funnel, under a nitrogen atmosphere.

The temperature was maintained at about 10° C. using an ice-water bath.

200 ml of the vitamin F chloride above was added dropwise while keeping the temperature at about 10° C. The reaction medium was then stirred for 2 hours at room temperature.

The pasty mixture obtained was diluted by adding 200 ml of dichloromethane. The resulting mixture was then washed several times: (i) addition of distilled water and removal of the upper aqueous solution, (ii) addition of 1 N hydrochloric acid solution and removal of the aqueous phase, (iii) addition of distilled water and removal of the aqueous phase.

The organic phase was dried over sodium sulphate and then filtered and concentrated to dryness.

A thick light-brown oil was obtained, which was dissolved in 350 ml of a water/trifluoroacetic acid mixture (at $11 \times 10^{-3}$ mol/liter) and left at room temperature for 1 hour. The mixture was concentrated and then taken up 5 times in 100 ml of toluene. The residue was purified on silica gel.

12 g of compound was obtained in the form of a yellow powder.

$^{13}$C NMR (DMSO) 200 MHz: δ (ppm): 60.76; 63.82, 92.10; 92.24; 96.75; 96.86

The $^1$H and $^{13}$C NMR spectra (DMSO) 200 MHz were in accordance with the expected structure.

EXAMPLE 3

Preparation of 3-O-octadeca-9,12-dienoyl-D-glucopyranose 29.6 g of diacetone-D-glucose dissolved in 200 ml of dichloromethane, and 26 ml of triethylamine, were introduced into a 500 ml three-necked flask on which was mounted a condenser and a dropping funnel, under a nitrogen atmosphere.

The temperature was maintained at about 10° C. using an ice-water bath.

200 ml of octadeca-9,12-dienoic (linoleic) acid chloride was added dropwise while maintaining the temperature at about 10° C. The reaction mixture was then stirred for 2 hours at room temperature.

The pasty mixture obtained was diluted by adding 200 ml of dichloromethane. The resulting mixture was then washed several times: (i) addition of distilled water and removal of the upper aqueous solution, (ii) addition of 1N hydrochloric acid solution and removal of the aqueous phase, (iii) addition of distilled water and removal of the aqueous phase.

The organic phase was dried over sodium sulphate and then filtered and concentrated to dryness.

21 g of a thick light-brown oil was obtained, which was dissolved in 350 ml of a water/trifluoroacetic acid mixture (at $11 \times 10^{-3}$ mol/liter) and left at room temperature for 1 hour. The mixture was concentrated and then taken up 5 times in 100 ml of toluene. The residue was purified on silica gel.

10.8 g of compound was obtained in the form of a yellow oil (64% yield).

The $^1$H and $^{13}$C NMR spectra (DMSO) 200 MHz were in accordance with the expected structure.

EXAMPLE 4

It is known that one solution for impeding the propagation of the process that leads to the excessive loss of hair is to use cosmetic active agents that are aimed at limiting the synthesis of mediators derived from the 5-lipoxygenase pathway, for example, leukotrienes. Lipoxygenase inhibitors fall within the category of these active agents.

The effect of the compounds of disclosed herein on the inhibition of purified soybean 15-lipoxygenase was thus tested, given that soybean 15-lipoxygenase is a study model commonly used as a predictive model for human 5-lipoxygenase.

The test performed was as follows:
preparation of a 100 mM, pH 7.5 Tris buffer solution
preparation of a suspension of purified soybean 15-lipoxygenase L1 (0.20 mg/ml) in a pH 7.5100 mM Tris buffer; storage in ice;
calibration of the oxymeter, tank equipped with a magnetic stirring system and thermostatically maintained at 25° C.;
preparation of an aqueous-alcoholic solution (absolute ethanol/water, 5/95, v/v) of potassium arachidonate at a concentration of 7.5 mM;
preparation of a solution of the test compound at a concentration of 30 mM in dimethyl sulphoxide (DMSO);
introduction into the oxymeter tank, with stirring, of 456.6 µl of buffer solution, 16.7 µl of potassium arachidonate solution and 16.7 µl of solution of the test compound or 16.7 µl of DMSO in the case of the "control" measurement.

The recorder was switched on and 10 µl of suspension of 15-lipoxygenase was introduced into the tank.

The maximum rate of consumption of oxygen (Vmax) was recorded.

The various Vmax values were compared with that of the control and the results were expressed as a % thereof. The test was repeated 10 times and an average of these 10 tests were determined.

The following compounds were tested:
A: 6-O-octadeca-9,12-dienoyl-D-glucopyranose
B: 6-O-octadeca-9-enoyl-D-glucopyranose
C: 6-O-octadecanoyl-D-glucopyranose
D: 6-O-hexadecanoyl-D-glucopyranose
E: 3-O-octadeca-9,12-dienoyl-D-glucopyranose
F: glucose ester of vitamin F (mainly ester in position 6)
G: glucose ester of vitamin F (mainly ester in position 3)

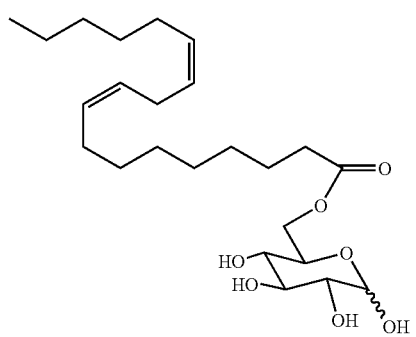

compound A

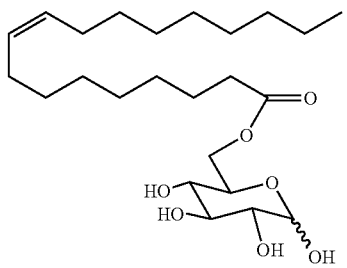

compound B

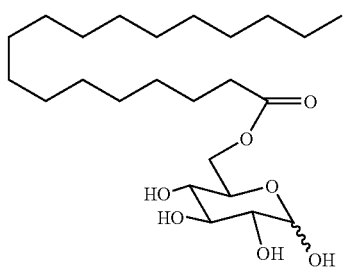

compound C

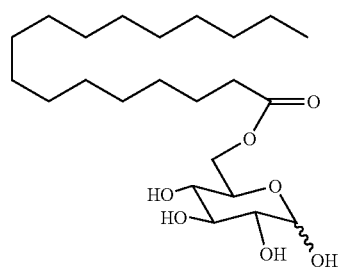

compound D

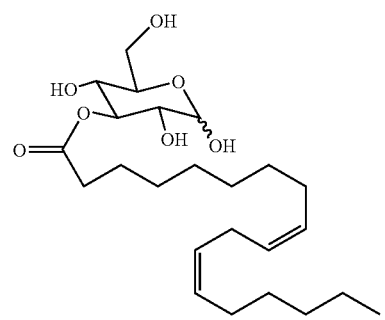

compound E

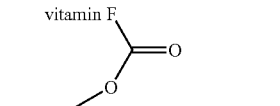

vitamin F compound F

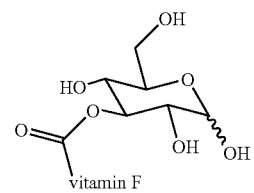

compound G vitamin F

The following results were obtained, expressed as a % of inhibition of the test compound (at a concentration of 1 mM) relative to the control:

| Compound | % of inhibition |
| --- | --- |
| Compound A | 71% |
| Compound B | 30% |
| Compound C | 49% |
| Compound D | 15% |
| Compound E | 80% |
| Compound F | 81% |
| Compound G | 86% |

It was thus found that the products disclosed herein (compounds F and G) have good capacity for inhibition of soybean lipoxygenase.

This capacity was even greater than that of the esters of glucose and of saturated or unsaturated $C_{18}$ acid, and also than that of the saturated $C_{16}$ ester.

This result is particularly surprising given the fact that it would have been expected that this mixture of "$C_{16}$ esters+ $C_{18}$ esters" (e.g., compound F or compound G) would have been less active than the $C_{18}$ esters alone.

EXAMPLE 5

The stability of the compounds disclosed herein were assessed (measured by the hydrolysis of the esters).

Solutions comprising 0.1% by weight of the compounds in an ethanol/isopropanol/water mixture (64/16/20 by volume) were prepared. These solutions were left in a chamber thermostatically maintained at 45° C. for 2 months.

The percentage of hydrolysed glucopyranose linoleate was then determined by HPLC.

The following results were obtained:

| Compound | % of hydrolysis |
| --- | --- |
| glucose ester of vitamin F (mainly ester in position 6) | 3% |
| 6-O-octadeca-9,12-dienoyl-D-glucopyranose | 7% |
| glucose ester of vitamin F (mainly ester in position 3) | 17% |
| 3-O-octadeca-9,12-dienoyl-D-glucopyranose | 30% |

It was thus found that the glucose esters of vitamin F have better stability than the glucose esters of linoleic acid.

Moreover, the stability of the ester in position 6 of glucose and of vitamin F was slightly better than that of the same ester esterified in position 3.

EXAMPLE 6

Daily Lotion

A composition comprising the constituents below was prepared:

| | |
| --- | --- |
| compound of Example 1 | 0.05 g |
| ethanol | 60 g |
| fragrance, colorants | qs |
| demineralised water | qs 100 g |

EXAMPLE 7

Liposomal Gel

A composition comprising the constituents below was prepared:

| | |
| --- | --- |
| compound of Example 2 | 0.5 g |
| carbomer | 0.25 g |
| triethanolamine | qs pH 7 |
| preserving agents | qs |
| demineralised water | qs 100 g |

EXAMPLE 8

Lotion for Preventing Hair Loss

A composition comprising the constituents below was prepared:

| | |
| --- | --- |
| compound of Example 1 | 1 g |
| propylene glycol | 10 g |
| isopropanol | qs 100 g |

1 ml of this lotion was applied at a rate of once or twice a day.

EXAMPLE 9

Lotion for Preventing Hair Loss

A composition comprising the constituents below was prepared:

| | |
| --- | --- |
| compound of Example 2 | 2 g |
| propylene glycol | 30 g |
| ethanol | 40.5 g |
| water | qs 100 g |

This lotion was applied once or twice a day, at a rate of 1-ml-per application.

EXAMPLE 10

Lotion for Preventing Hair Loss

A composition comprising the constituents below was prepared:

| | |
| --- | --- |
| compound of Example 2 | 1 g |
| propylene glycol monomethyl ether (Dowanol PM from Dow) | 20 g |
| hydroxypropylcellulose (Klucel G from Hercules) | 3 g |
| ethanol | 40 g |
| water | qs 100 g |

This thickened lotion was applied once or twice a day, at a rate of one ml per application.

EXAMPLE 11

Lotion for Preventing Hair Loss

A composition comprising the constituents below was prepared:

| | |
|---|---|
| compound of Example 1 | 0.2 g |
| pyrimidine 3-oxide (Aminexil) derivative | 1.5 g |
| water | qs 100 g |

EXAMPLE 12

Antidandruff Shampoo

A shampoo was prepared, comprising:

| | |
|---|---|
| compound of Example 1 | 1.2 g |
| salicylic acid | 2 g |
| polyglyceryl 3-hydroxylauryl ether | 26 g A.M. |
| hydroxypropylcellulose (Klucel G from Hercules) | 2 g |
| preserving agent | 50 g |
| triethanolamine | qs pH 7.5 |
| Water | qs 100 g | wherein "A.M" means active material.

This shampoo was used daily at a rate of 10 g per head of hair with an action time of the order of 1 minute, and was applied over a period of 2 weeks. A rapid drop in the sensations of pruritus and a marked improvement in the dandruff condition were observed.

EXAMPLE 13

Antidandruff Lotion

A composition was prepared comprising:

| | |
|---|---|
| compound of Example 2 | 0.3 g A.M. |
| octopirox (piroctone olamine) | 0.2 g |
| ethanol | 30 g A.M. |
| water | qs 100 g | wherein "A.M." means active material.

This solution was applied daily at a rate of 6 ml, and was applied for 1 to 2 weeks. A marked improvement in the dandruff condition was then observed.

EXAMPLE 14

Preparation of 6-O-oleoylglucose 6.02 g of trimethylacetyl chloride and 50 ml of tetrahydrofuran were introduced into a 250 ml three-necked flask. A mixture of 14.1 g of oleic acid and 5.05 g of triethylamine diluted in 50 ml of tetrahydrofuran was added slowly, under an inert atmosphere and at 0° C. The mixture was stirred for 1 hour and the salts formed were then filtered off to obtain a solution.

36 g of glucose were dissolved in 400 ml of pyridine in a 1 liter three-necked flask, and the above solution was added thereto, under an inert atmosphere, at room temperature; stirring was continued overnight.

The reaction medium was evaporated to dryness under vacuum to remove the pyridine, the paste obtained was then extracted (water/organic solvent mixture) and the recovered organic phase was dried, filtered and evaporated.

19.5 g of a white solid (87% yield) of O-oleoylglucose was obtained.

The $^{13}$C NMR and mass spectrum analyses were in accordance with the expected structure.

EXAMPLE 15

Preparation of 6-O-linoleoylglucose 6.02 g of trimethylacetyl chloride and 50 ml of tetrahydrofuran were placed in a 250 ml three-necked flask. A mixture of 14 g of linoleic acid and 5.05 g of triethylamine diluted in 50 ml of tetrahydrofuran was added slowly, under an inert atmosphere and at 0° C. The mixture was stirred for 1 hour and the salts formed were then filtered off to obtain a solution.

36 g of glucose was dissolved in 400 ml of pyridine in a 1 liter three-necked flask, and the above solution was added thereto, under an inert atmosphere, at room temperature; stirring was continued overnight.

The reaction medium was evaporated to dryness under vacuum to remove the pyridine, the paste obtained was then extracted (water/organic solvent mixture) and the recovered organic phase was dried, filtered and evaporated.

18.7 g of a yellow paste (82% yield) of O-linoleoylglucose was obtained.

The yield of 6-O-linoleoylglucose was 62%.

The $^{13}$C NMR and mass spectrum analyses were in accordance with the expected structure.

What is claimed is:

1. A process for preparing at least one 0-acyl derivative mainly in position 6 of glucose chosen from derivatives of formula (Ia) below:

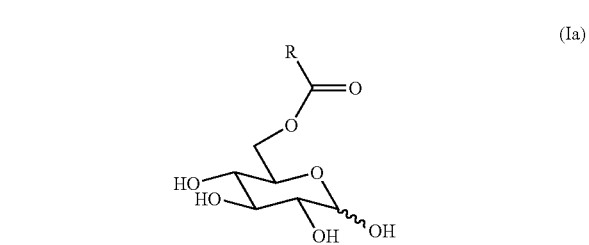

R is chosen from linear and branched, saturated and unsaturated hydrocarbon-based chains comprising from 7 to 21 carbon atoms, comprising:

(1) preparing a mixed anhydride of formula (II):

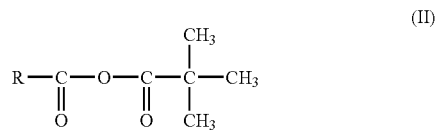

by reacting a carboxylic acid of formula R—COOH with a trimethylacetic acid halide of formula X—C(O)—C(CH$_3$)$_3$, wherein X is chosen from chlorine and bromine, and (2) reacting said mixed anhydride formed with glucose;

wherein in the compounds of formula (Ia), the ratio of the number of ester functional groups in position 6 to the total number of ester functional groups, per glucose molecule, ranges from 55% to 95%.

2. The process according to claim 1, wherein the R is chosen from linear and branched, saturated and unsaturated hydrocarbon-based chains comprising from 11 to 17 carbon atoms.

3. The process according to claim 1, wherein the acyl residue—COR is chosen from at least one of octanoyl, decanoyl, dodecanoyl, myristoyl, hexadecanoyl, stearoyl, palmitoleoyl, oleoyl, linoleoyl and linolenoyl residues.

4. The process according to claim 1, wherein the carboxylic acid is chosen from at least one of octanoic acid, decanoic acid, dodecanoic acid, myristic acid, hexadecanoic acid, stearic acid, oleic acid, linoleic acid and linolenic acid.

5. The process according to claim 1, wherein at least one of the reactions (1) and (2) is performed in an organic reaction solvent chosen from at least one of tetrahydrofuran, N,N-dimethylformamide, N-methylpyrrolidone, pyridine and toluene.

6. The process according to claim 1, wherein the reaction (1) is performed in the presence of at least one base chosen from triethylamine, pyridine, 4-dimethylaminopyridine, tributylamine and N-methylmorpholine.

7. The process according to claim 1, wherein from 0.3 to 3 equivalents of the carboxylic acid are reacted with 1 equivalent of the trimethylacetyl halide.

8. The process according to claim 7, wherein from 0.5 to 1.5 equivalents of the carboxylic acid are reacted with 1 equivalent of the trimethylacetyl halide.

9. The process according to claim 1, wherein from 0.5 to 1.5 equivalent of the mixed anhydride is reacted with 3 equivalents of the glucose.

10. The process according to claim 9, wherein from 0.9 to 1.1 of the mixed anhydride is reacted with 3 equivalents of the glucose.

11. The process according to claim 10, wherein 1 equivalent of the mixed anhydride is reacted with 3 equivalents of the glucose.

12. The process according to claim 11, wherein the ratio of the number of ester functional groups in position 6 to the total number of ester functional groups, per glucose molecule ranges from 60% to 80%.

13. The process according to claim 12, wherein the ratio of the number of ester functional groups in position 6 to the total number of ester functional groups, per glucose molecule ranges from 68 to 75%.

14. The process according to claim 1, wherein the at least one 0-acyl derivative is chosen from 6-O-octadeca-9,12-dienoyl-D-glucopyranose; 6-0-octadeca-9-enoyl-D-glucopyranose; 6-O-octadecanoyl-D-glucopyranose; and 6-0-hexadecanoyl-D-glucopyranose.

15. The process according to claim 1, wherein a yield of at least about 70% of the at least one O-acyl derivative of glucose is obtained.

* * * * *